(12) United States Patent
Kirkup et al.

(10) Patent No.: US 6,175,762 B1
(45) Date of Patent: Jan. 16, 2001

(54) EEG BASED ACTIVATION SYSTEM

(75) Inventors: Leslie Kirkup, Summer Hill; Andrew Peter Searle, Stanmore; Paul Francis McIsaac, Carlingford; Ashley Ronald Craig, Gosford, all of (AU)

(73) Assignee: University of Technology, Sydney, Haymarket (AU)

( * ) Notice: Under 35 U.S.C. 154(b), the term of this patent shall be extended for 0 days.

(21) Appl. No.: 09/155,802

(22) PCT Filed: Apr. 10, 1997

(86) PCT No.: PCT/AU97/00227

§ 371 Date: Oct. 6, 1998

§ 102(e) Date: Oct. 6, 1998

(87) PCT Pub. No.: WO97/37590

PCT Pub. Date: Oct. 16, 1997

(30) Foreign Application Priority Data

Apr. 10, 1996 (AU) .................................................. PN9189
Aug. 16, 1996 (AU) .................................................. PO1700
Nov. 26, 1996 (AU) .................................................. PO3859

(51) Int. Cl.[7] ........................................................ A61B 5/04
(52) U.S. Cl. ................................................................ 600/544
(58) Field of Search ...................................... 600/544, 545, 600/546

(56) References Cited

U.S. PATENT DOCUMENTS 4,354,505  10/1982  Shiga ..................................... 128/732
5,279,305   1/1994  Zimmerman et al. ................ 128/731
5,817,030 * 10/1998  Tarjan et al. .......................... 600/544

FOREIGN PATENT DOCUMENTS 0177075     4/1986  (EP) .
0632421     1/1995  (EP) .
WO89/09019 10/1989  (WO) .

OTHER PUBLICATIONS

J.R. Wolpaw et al, "An EEG–Based Brain–Computer Interface for Cursor Control", Electroencephalography and Clinical Neurophysiology, vol. 78, No. 3, Mar. 1, 1991, pp. 252–259.

* cited by examiner

Primary Examiner—Scott M. Getzow
(74) Attorney, Agent, or Firm—Christie, Parker & Hale, LLP

(57) ABSTRACT

The invention concerns an EEG based activation system that may be used to turn an appliance ON or OFF. EEG signals have been used for control purposes using biofeedback methods. However, the drawbacks of this are the learning time required by a subject which may take days or months. The present invention provides a simplified EEG based system for activation of an appliance. The system has an input port to receive electrical signals from scalp electrodes (2, 3), an amplifier (5) to amplify the signals, a bandpass filter (6) to filter the signals and a signal averager (8) to smooth out the signals. Furthermore, the signal averager integrates any received signal in the passband of the filter and provides a ramping output, and the integrating time constant being between one and five seconds.

11 Claims, 5 Drawing Sheets

EEG BASED ACTIVATION SYSTEM

BACKGROUND OF THE INVENTION

1. Technical Field

This invention concerns an EEG based activation system that may be used to turn an appliance or device ON or OFF. The system may also be used to provide proportional control, which could be used, for example, to vary the sound level output of a TV or stereo sound system.

2. Background Art

Considerable interest surrounds the detection, analysis and utilization of electrical signals generated within the brain. The detection and analysis of such signals by using electrodes pressed against the scalp to sense the signals is generally referred to as electroencephalography (EEG). The application of EEG to assist in medical diagnosis and in biofeedback studies is well established. Biofeedback using EEG, in which subjects may modify their EEG waveform in response to some visual stimulus, offers promise in control applications. Powerful signal processing tools such as artificial neural networks, are being incorporated to improve the reliability of similar systems.

Though significant advances in the utilization of EEG signals for control purposes through biofeedback methods have been made in recent years, a number of difficulties remain. In situations where the control of components in the EEG waveform must be learned, the training time using biofeedback methods may span from days to months. Not all subjects are capable of learning control through biofeedback and others are unable to transfer a learned effect out of a laboratory situation. Additionally, many low impedance contacts may need to be made to the scalp to sense EEG signals. This is time consuming, attracts user hostility, and over time 'good' electrical contact between one or more electrodes and the scalp may become impaired.

SUMMARY OF THE INVENTION

The present invention, as currently envisaged, provides an EEG based activation system. The system has an input port to receive electrical signals from scalp electrodes, an amplifier to amplify the signals, a bandpass filter to filter the signals and a signal averager to smooth out the signals. The speed and reliability of the system are provided by the signal averager which integrates any received signal in the passband of the filter and provides a ramping output. The integrating time constant may be between 1 and 5 seconds, and is advantageously around 2 seconds to give a tradeoff between spurious switching and switching delay.

The EEG based activation system is electronic technology which allows a person to rapidly and remotely control electronics devices or appliances in the environment using their brain signals. The system requires no training and the self controlled signal that is harnessed by the system is highly reliable and reproducible. It is not based on biofeedback principles and no training is required to operate the system.

The bandpass filter passes signals in the alpha-band, between 8 and 13 Hz, since human subjects consistently show an increase in alpha activity upon eye closure. The filter advantageously passes signals in the range 9 to 11 Hz since these signals show a consistent change in average level when the eyes are opened and closed.

A comparator may compare the smoothed signal with a reference and provide an output signal that changes state whenever the smoothed signal exceeds a predetermined threshold. The reference will generally be derived through trial and error. As the output voltage from the signal averager increases approximately linearly with time, the system can be adapted for multi-level switching or even proportional control.

A noise protection module may receive the signals from the electrodes and extract a noise band using another bandpass filter. This noiseband signal may also be averaged, and then be used to freeze the output of the activation system when the averaged noise signal exceeds a predetermined threshold. The noiseband may be between 27 to 29 Hz to pick up noise due to head movement and teeth grinding.

Embodiments of this system allow a person to activate an electrical appliance or device through self-control of EEG signals without the training that biofeedback requires. In a preferred form it involves a subject closing their eyes, opening their eyes or both opening and closing their eyes. Indications are that in excess of 90% of the adult population is able to effect this control.

The system may be made insensitive to sources of interfering signals such as eye movement, blinking or external electromagnetic interference.

BRIEF DESCRIPTION OF THE DRAWINGS

An example of the invention will now be described with reference to the accompanying drawings, in which.

DETAILED DESCRIPTION OF THE INVENTION

Figure 1:
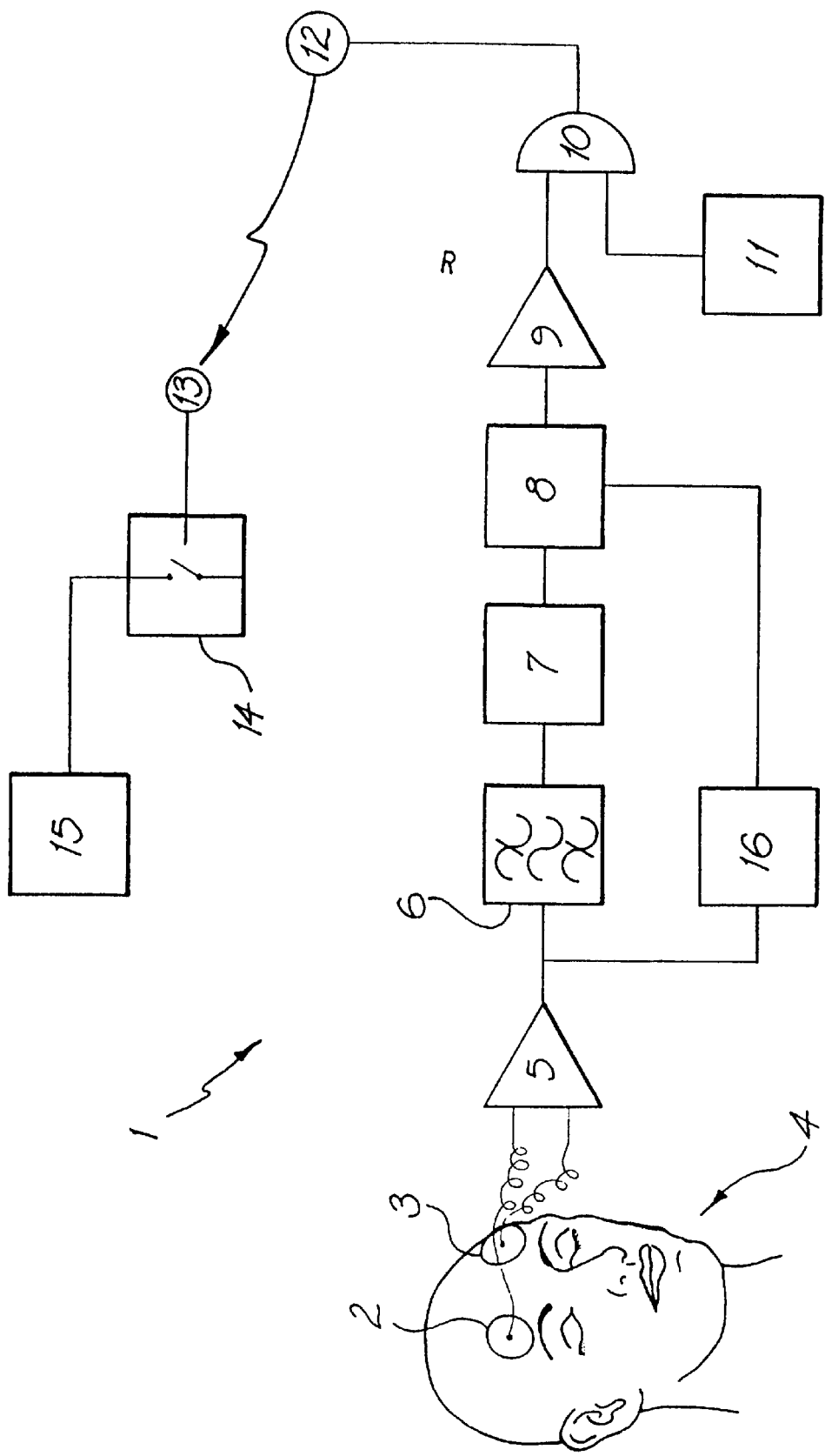
FIG. 1 is a block diagram of an EEG based activation system embodying the present invention.

Referring to FIG. 1, the system 1 comprises two conventional silver-silver chloride electrodes 2 and 3 configured in differential (bipolar) mode. The electrodes smeared with conducting gel are pressed against the scalp of a subject 4, for instance, in the O1–T5 positions, as given by the international 10–20 position classification system. A differential EEG signal is produced and then amplified using an amplifier 5 with gain of 74 dB.

The next stage consists of an analogue bandpass filter 6 centered in the alpha band, with a centre frequency of 10 Hz and a bandwidth of 2 Hz. The bandlimited signal is converted to DC using an RMS to DC converter 7.

A signal averager 8 follows the RMS to DC converter 7 to smooth out the rapid variations caused by the aperiodic nature of the alpha activity. The averager consists of a signal integrator that delivers a ramping up output when an input signal is received in the pass-band of filter 6. When the input signal is removed, the output of the averager slowly falls.

Figure 2:
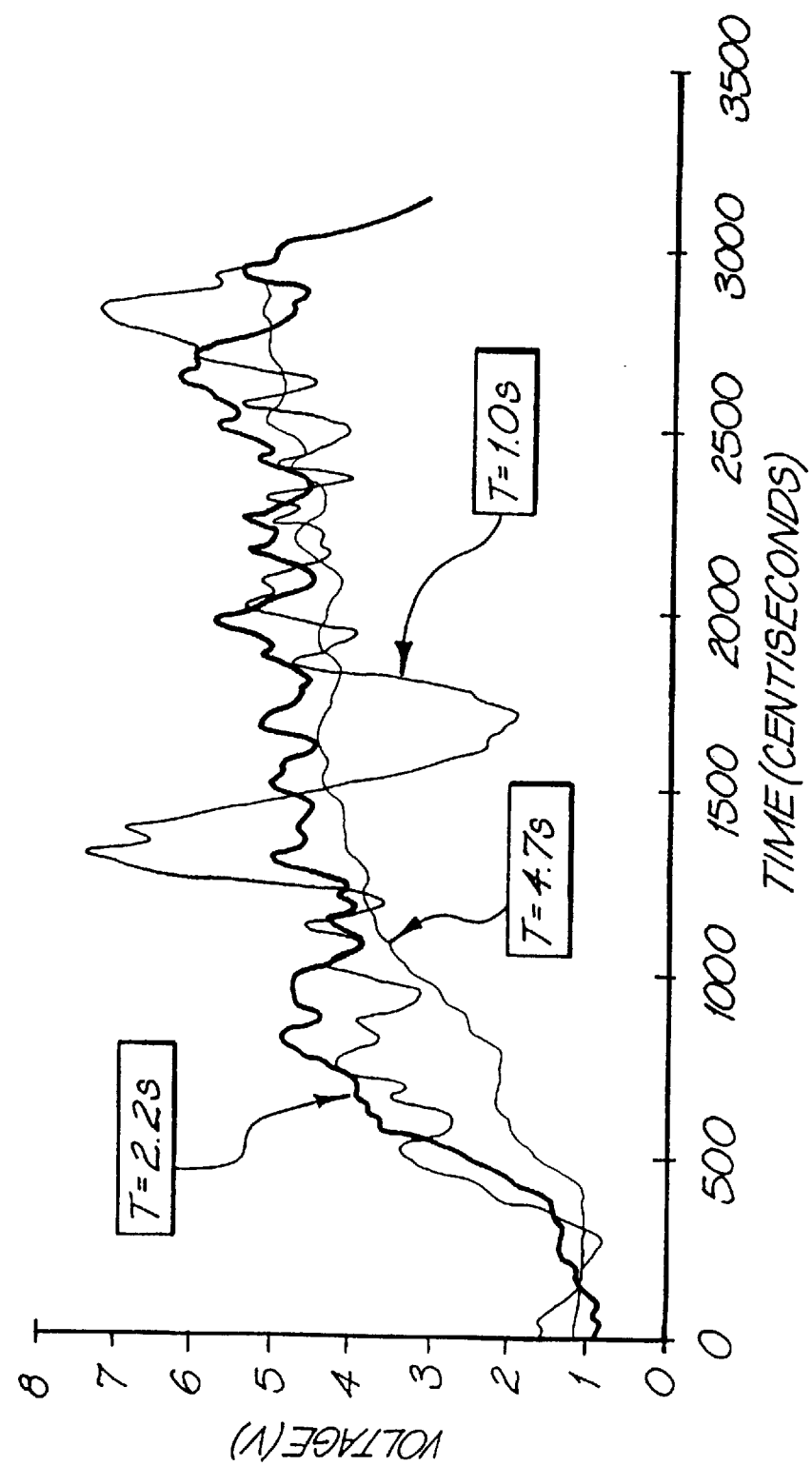
FIG. 2 is a graph showing the amplified output of a signal averager within the system of FIG. 1, for three different time constants, 1 s, 2.2 s and 4.7 s.

FIG. 2 shows the amplified output of the signal averager 8 for three characteristic time constants T, namely where T is 1 second, 2.2 seconds and 4.7 seconds. The rapid variations likely to cause spurious switching are not transferred from the input to the output of the averager 8. A 2.2 second time constant offers an acceptable compromise between rapid switching (less than 3 s) while effectively eliminating rapid variations at the output.

The output from the averager 8 is further amplified by amplifier 9, having a gain of 34 dB, and is then presented to one input of a comparator 10. The other input to comparator 10 is connected to a predetermined DC threshold voltage 11. The threshold voltage $V_{th}$ is between 0.5 V and 1 V higher than the nominal voltage at the other input of the comparator when a subject has his eyes open. The noise immunity provided by the comparator 10 prevents spurious switching that might be caused by natural variations in the alpha signal amplitude.

The EEG signals generated in, for instance, the occipital-temporal regions of the brain are continuously monitored by the apparatus described. When the signal amplitude at 10 Hz (bandwidth of 2 Hz) increases beyond the predetermined threshold set by comparator 10, during eye closure, an infra red transmitter 12 is activated. An infra red receiver 13 responds by toggling a switch 14 attached to an electrical appliance 15.

The switch 14 is toggled only when the signal from amplifier 9 rises up above the predetermined threshold 11 and not as it falls below the threshold from above. It follows that the state of the switch is not altered when a person opens his/her eyes.

Most EEG signals suffer from artefacts, which can be caused, for example, by muscle or eye movement, generally referred to as electromyograph (EMG) or electrooculogram (EOG) respectively. As long as the spectral components of signals that would interfere or corrupt the EEG spectrum, lie outside the 9 to 11 Hz frequency interval of interest here, high order low or high pass filters can be used to attenuate the interference. EMG artefact has most of its energy concentrated above 15 Hz. Nevertheless, the artefact does affect the complete EEG spectrum.

FIG. 1 shows a switching protection module 16 connected between the output of amplifier 5 and the signal averager 8, to address the problem of signal artefacts.

The switching suppression module 16 monitors the signal amplitude at the output of amplifier 5, at a frequency known to be dominant when interfering signals, such as those due to EMG, occur. While the signal amplitude exceeds a predetermined threshold, the output of the comparator 10 is prevented from changing state. In effect the output is 'frozen' until the amplitude of the noise component relaxes below the threshold level, at which time the comparator 10 is again responsive to changes in the EEG signal amplitude.

Figure 3:
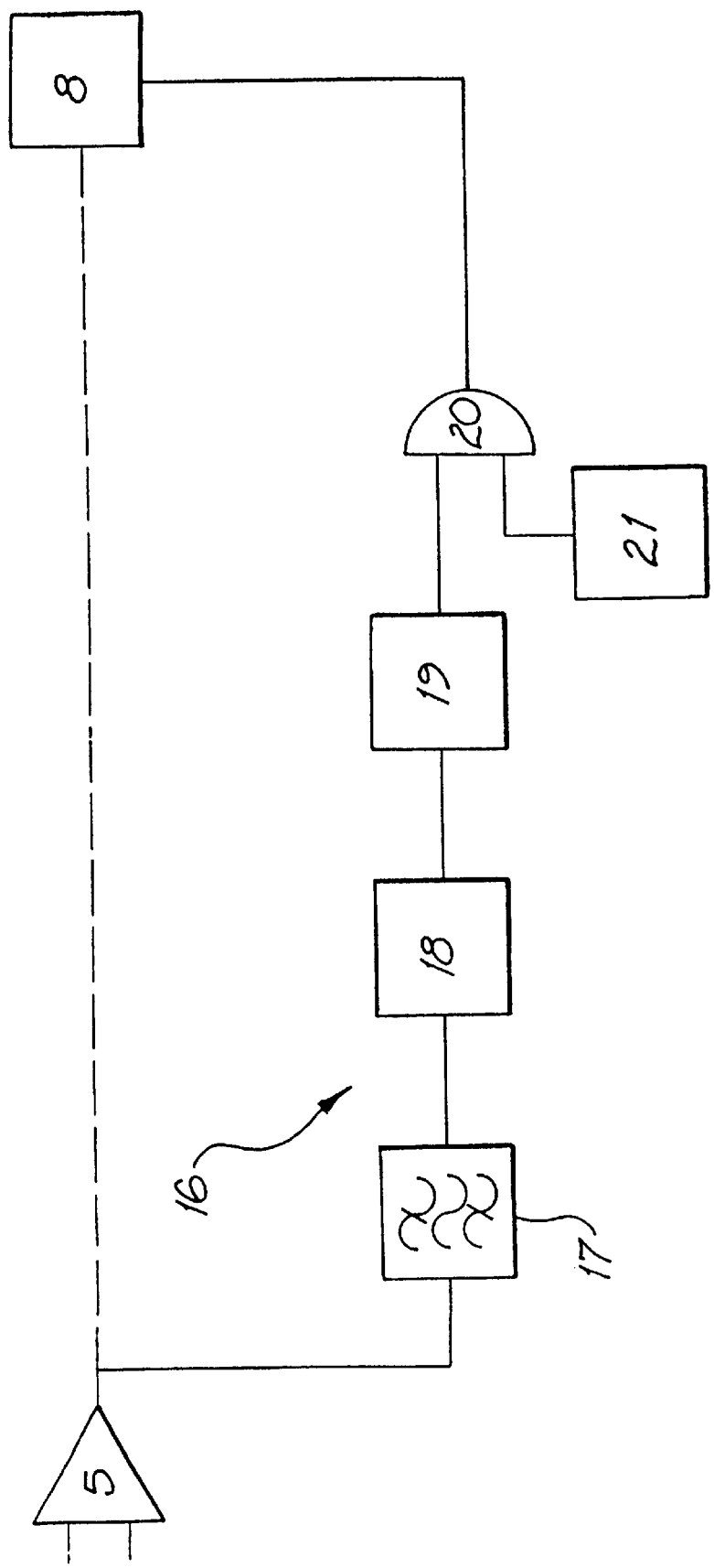
FIG. 3 is a block diagram of a noise protection module used with an embodiment of the present invention.

FIG. 3 shows the noise protection module 16 in greater detail. The output of the amplifier 5 of gain 74 dB shown in FIG. 1 is fed to a bandpass filter 17 with a centre frequency of 28 Hz and a bandwidth of 2 Hz. The bandlimited signal is converted to DC using an RMS to DC converter 18. A signal averager 19 follows the RMS to DC converter 18 to smooth the signal. After AC to DC conversion and time averaging, the 'noise' signal is fed to one input of a comparator 20. The other input to the comparator 20 is set to a noise threshold value 21. The threshold value is chosen by trial and error so that it is effective in suppressing switching when EMG levels are large enough to cause spurious switching.

When wideband noise exists, the amplitude of the 28 Hz component of the signal sensed by the electrodes increases. When the noise signal exceeds the noise threshold, the comparator 20 switches states and in doing so forces the output of the signal averager 8 appearing in FIG. 1 to go low. This effectively prevents the output of the comparator 10 in FIG. 1 from going high, thereby suppressing further on-off toggling of an appliance or device 15. The output remains 'frozen' until the noise signal presented to comparator 20 drops below the noise threshold value.

Experimental Results

In order to establish the capability of the system, all experiment was conducted in which a male subject was asked to successively activate a switch by closing his eyes. The time taken between issuing the command and the switch activation was recorded. The quiescent eyes open voltage for the subject was 0.7 V and the switching threshold of the comparator was set to 1.2 V. The subject was asked to remain as still as possible for the duration of the experiment.

Figure 4:
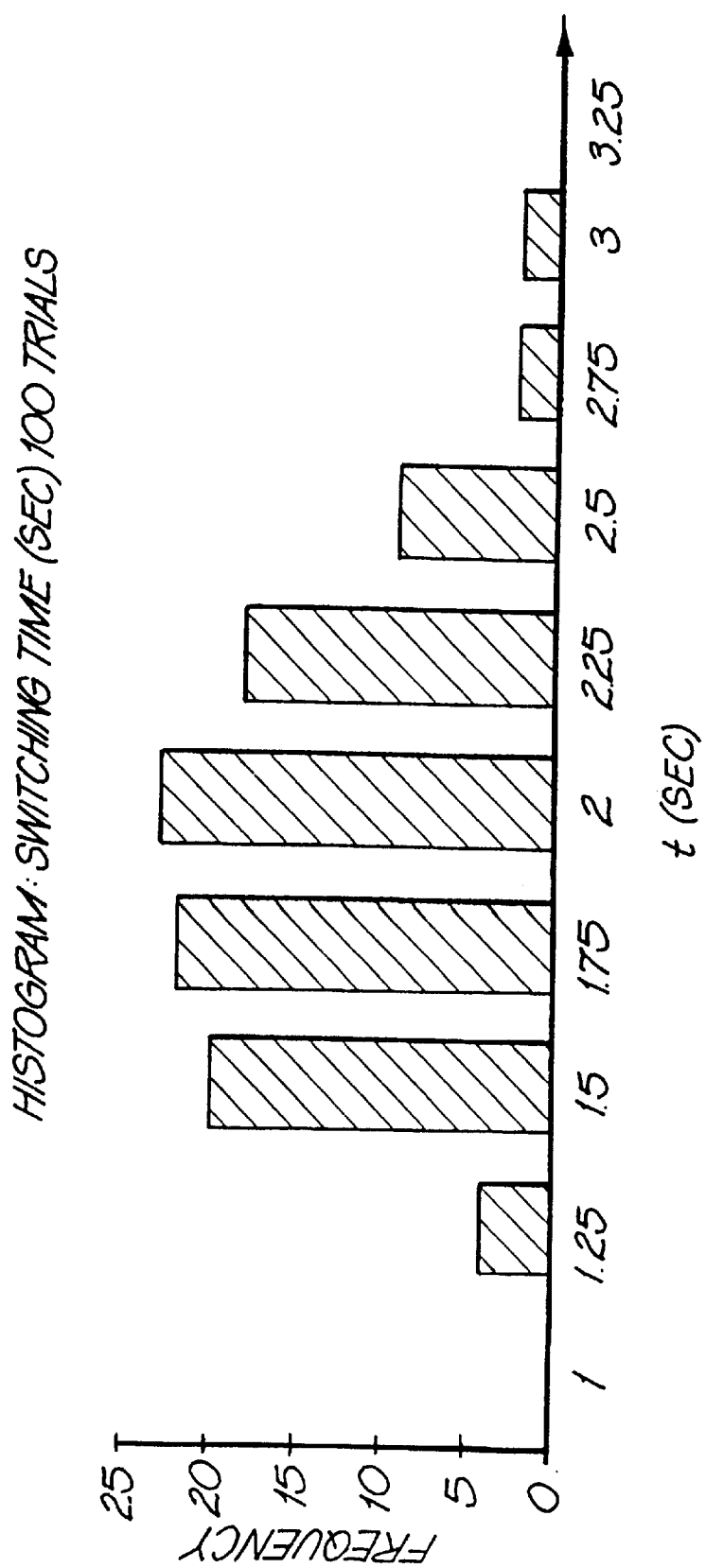
FIG. 4 is a histogram showing the frequency of the time taken for switch activation over a hundred trials.

FIG. 4 is a histogram of the results of one hundred successive activations of the switch. The histogram shows the frequency of the times taken to exceed the threshold and activate the switch. In this experiment the minimum activation time is 1.3 seconds and the maximum 3.2 seconds. The mean-activation time is 2.0 seconds with a standard deviation of 0.4 seconds.

Figure 5:
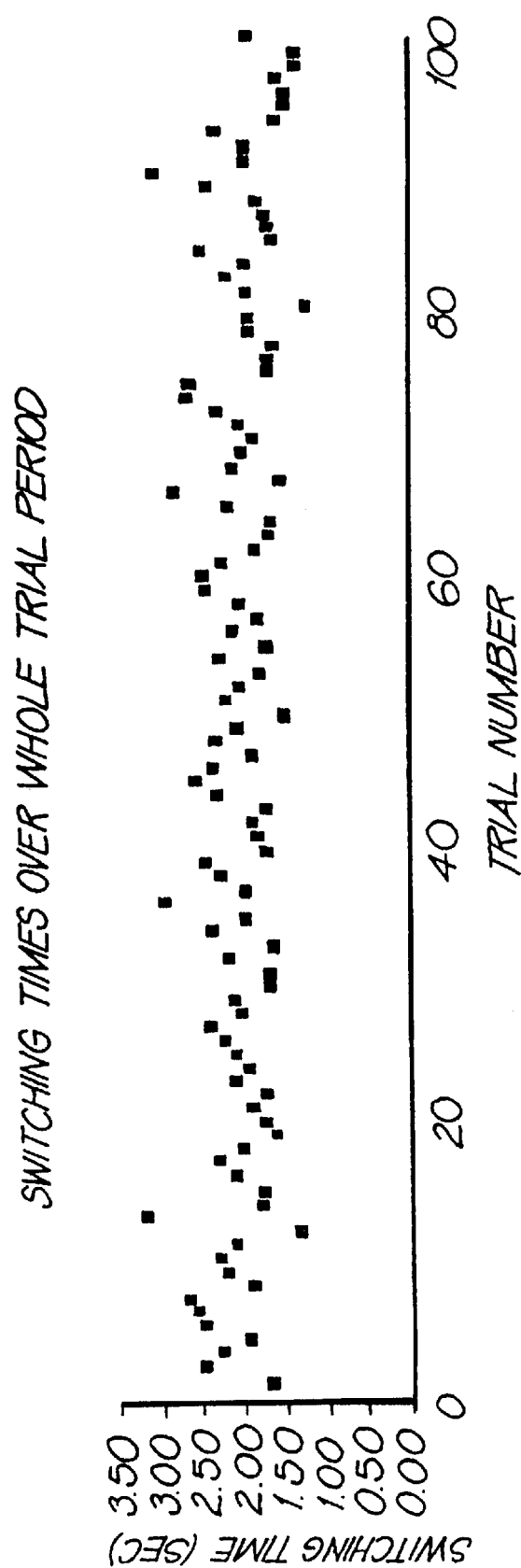
FIG. 5 is a graph showing the time for switch activation as a function of trial number.

FIG. 5 shows the time for switch activation as a function of trial number. Trend analysis of the data, which was gathered over a period of 30 minutes, suggests that, over the duration of the experiment, the activation time is marginally improved by repeated attempts to activate the switch. The correlation between switching time and trial number is −0.21, with the improvement statistically significant at the 5% level. It was observed during this experiment and others carried out subsequently with other subjects, that eye motion or blinking are not causes of spurious switching.

A longitudinal study with this subject was carried out over a period of 18 months to determine the quiescent voltages. The quiescent eyes open voltage, at the input to the comparator varied in the range 0.7 V to 1.1 V. The quiescent eyes closed voltage varied from 3 V to 4 V. This suggests that the comparator threshold voltage for this subject should be set at around 1.6 V to 2 V.

The average time for switching to occur after eye closure is related to the difference between the comparator threshold voltage, $V_{th}$, and the quiescent eyes open voltage, $V_{qeo}$. The mean time for switching to occur can be considered as a function of V, where, $$V=V_{th}-V_{qeo}$$

To a first approximation, the voltage V and the time taken to reach that voltage with the eyes closed t, may be related by:

$$V=V_{max}(1-\exp(-t/\tau)) \qquad [1]$$

where $V_{max}$ is the maximum time averaged voltage above $V_{qeo}$ that a subject can generate; and $\tau$ is the time constant for the voltage rise that depends on both the time constant of the signal averager as well as the characteristic rise time of the alpha signal amplitude upon eye closure.

There is some delay, or offset, $t_{offset}$, between the subject being instructed to close his eyes and the alpha signal amplitude beginning to rise.

Rearranging Equation [1] and including the offset we get, $$t=-\tau \ln(1-(V/V_{max}))+t_{offset} \qquad [2]$$

Fitting Equation [2] to experimentally recorded data using a weighted nonlinear least squares fitting routine gives:

$$\tau=(3.1\pm0.4)s,\ V_{max}=(3.16\pm0.9)V,\ t_{offset}=(1.52\pm0.19)s$$

For any preferred switching time, t, it is possible to establish to what value of threshold voltage $V_{th}$ must be set for this subject by using equation [2] to find V. The threshold voltage $V_{th}$ is set to $V_{qeo}+V$.

The effectiveness of the noise protection module 16 was established in two ways. First, a schedule of movements and actions likely to cause spurious switching was devised. This consisted of a sequence of 10 second intervals of, for example, grinding teeth followed by remaining still and followed by head nodding. Proper operation of the system was confirmed before and after the sequence by the subject remaining still and activating the switch through eye closure. Table 1 shows the sequence of actions as well as the occurrence (or otherwise) of spurious switching with the noise protection module both active and inactive:

TABLE 1

SPURIOUS SWITCHING: OCCURENCE = 1, NONE = 0

| ACTION | SUPPRESSION OFF | SUPPRESSION ON |
| --- | --- | --- |
| none | 0 | 0 |
| grinding teeth | 1 | 0 |
| none | 1 | 0 |
| nodding head | 1 | 0 |
| none | 0 | 0 |
| rotating head | 1 | 0 |
| none | 0 | 0 |
| yawning | 1 | 0 |
| none | 0 | 0 |
| rapid blinking | 1 | 0 |
| none | 0 | 0 |
| raising eyebrows | 1 | 0 |
| none | 0 | 0 |
| jiggling cable | 1 | 0 |
| TOTAL | 8 | 0 |

The threshold 11 for switching on the system was set to 2 V. With the noise protection module active no spurious switching occurred. With the module inactive, several false positives, such as switching not caused by eye closure, were recorded.

The behaviour of the system and the module was also assessed in a situation closer to that which might be encountered in use, for example in an office environment. The subject was asked to engage in 'normal' behaviour for 15 minutes, that is, no defined tasks were prescribed. During this time the subject spoke, turned his head, wrote, and answered the telephone. With the noise protection module inactive, 34 false positives were recorded in the 15 minute period. With the module active, no false positives were recorded in the next 15 minute period and the number of occasions the noise threshold of the module was exceeded was 77. It should be noted that not all artefacts large enough to trigger the noise protection module will necessarily cause spurious switching of the system.

It should be appreciated that, although the invention has been described with reference to a particular embodiment, it could be embodied in many other forms. In particular it should be understood that the invention is not limited to merely providing a single pulse output, and the ramping output of the signal averager may be used to activate a selective series of outputs as it ramps through different levels.

Individual eye closed to eye open signal variation ranges from 2:1 to 13:1, however, 3:1 is of sufficient magnitude to permit an individual to effect proportional control over external devices by deliberately varying the magnitude of their EEG signal; that is, turn on, speed up (or change channel), slow down, and turn off. The voltage generated upon eye closure (after amplification, filtering at 10 Hz and averaging of the "raw" EEG signal) is found to increase approximately linearly from about 1 V to 4 V. By setting other comparator levels between 1 V and 4 V, it is possible to offer multi-switching options. A person can activate one of six options in around 10–12 seconds. The 10–12 seconds needed to switch in the six option system is due to the cycling through the six options. After eye closure, the voltage increases to an upper threshold level at which point a sequence of options is activated and presented to the person in a step by step manner. The person now opens their eyes and waits for the device to be activated to be offered. When this occurs the person closes their eyes and the voltage increases until it reaches a lower threshold level at which point the desired device or appliance is activated. Typically, the upper threshold level will be set at 3 V and the lower threshold at 2 V. In order to test the effectiveness of this system, two persons (one male and one female) were required to select an appliance from the six options 30 times (random selection of a fan, a television, a radio, a light, a computer and an air conditioner). The time taken to select the option and the number of errors (selecting the wrong option) were recorded. Both persons were given a brief introduction and 15 minutes experience with the system before the trials. The first subject (male) correctly selected 27 of the 30 options in a mean time of 12 seconds per selection (standard deviation=2.1, minimum=8.5, maximum=16.3 seconds). The results demonstrate that repeated exposure improves the switching skills involved. Repeated practice should improve the error rate and reduce the time down to around 10 seconds, and the time could be reduced to around 5 seconds to select an option.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An EEG based activation system for providing an activation for equipment, comprising:

an input port to receive electrical signals from scalp electrodes;

an amplifier for amplifying the signals received at the input port;

a bandpass filter for filtering signals from the amplifier;

a signal averager for smoothing signals from the filter; and a comparator for receiving a signal from the signal averager;

wherein the signal averager integrates the signals in a passband from the bandpass filter and provides a ramping output, the signal averager has an integrating time constant of between one and five seconds, and the comparator compares the signal from the signal averager with a reference and provides an output signal that changes state whenever the signal from the signal averager exceeds a predetermined threshold in order to provide such activation in response to changes in the electrical signals received at the input port from the scalp electrodes.

2. The EEG based activation system according to claim 1 wherein the integrating time constant is around 2 seconds.

3. The EEG based activation system according to claim 1 wherein the bandpass filter passes the signals from the amplifier in the alpha-band, between 8 and 13 Hz.

4. The EEG based activation system according to claim 3 wherein the bandpass filter passes the signals from the amplifier in the range 9 to 11 Hz.

5. The EEG based activation system according to claim 1 wherein the reference is derived through trial and error.

6. The EEG based activation system according to claim 1 wherein the ramping output from the signal averager increases approximately linearly with time, and the system is adapted for multi-level switching proportional control.

7. The EEG based activation system according to claim 1 further comprising a noise protection module receiving the electrical signals from the scalp electrodes and extracting a noiseband signal using another bandpass filter, the noiseband signal is averaged by the signal averager, and used to freeze the output of the activation system when the averaged noiseband signal exceeds a predetermined threshold.

8. The EEG based activation system according to claim 7 wherein the noiseband signal is between 27 to 29 Hz.

9. A method of activating equipment using the system of claim 1 comprising the step of the subject wearing the scalp electrodes closing their eyes so that changes in the electrical signals received at the input port from the scalp electrodes cause a chance of state in the output signal to provide such activation.

10. A method of activating equipment using the system of claim 1 comprising the step of the subject wearing the scalp electrodes opening their eyes so that changes in the electrical signals received at the input port from the scalp electrodes cause a change of state in the output signal to provide such activation.

11. A method of activating equipment using the system of claim 1 comprising the step of the subject wearing the scalp electrodes closing and opening their eyes so that changes in the electrical signals received at the input port from the scalp electrodes cause a change of state in the output signal to provide such activation.

* * * * *